US010614412B2

(12) United States Patent
Broninx (10) Patent No.: US 10,614,412 B2
(45) Date of Patent: Apr. 7, 2020

(54) TRACEABILITY OF SURGICAL INSTRUMENTS IN A HOSPITAL ENVIRONMENT (71) Applicant: ANALYTIC—TRACABILITE HOSPITALIERE, Denain (FR)

(72) Inventor: Geoffrey Broninx, Neuville-sur-Escaut (FR)

(73) Assignee: ANALYTIC-TRACABILITE HOSPITALIERE, Denain (FR)

( * ) Notice: Subject to any disclaimer, the term of this patent is extended or adjusted under 35 U.S.C. 154(b) by 618 days.

(21) Appl. No.: 14/782,960

(22) PCT Filed: Apr. 10, 2014

(86) PCT No.: PCT/FR2014/050863
§ 371 (c)(1),
(2) Date: Oct. 7, 2015

(87) PCT Pub. No.: WO2014/167252
PCT Pub. Date: Oct. 16, 2014

(65) Prior Publication Data
US 2016/0042130 A1 Feb. 11, 2016

(30) Foreign Application Priority Data

Apr. 10, 2013 (FR) ...................... 13 53240

(51) Int. Cl.
*G16H 40/40* (2018.01)
*G06Q 10/08* (2012.01)
(Continued)

(52) U.S. Cl.
CPC ........... *G06Q 10/087* (2013.01); *A61B 90/90* (2016.02); *G06F 16/2358* (2019.01);
(Continued)

(58) Field of Classification Search
CPC ..................... G16H 40/40; G06Q 10/0875
See application file for complete search history.

(56) References Cited

U.S. PATENT DOCUMENTS 6,036,298 A * 3/2000 Walker ............... B41J 2/125
347/19
6,068,102 A * 5/2000 Kawase ............... G07D 5/02
194/317
(Continued)

FOREIGN PATENT DOCUMENTS

DE 20 2011 050 001 U1 7/2011
EP 2 581 863 A1 4/2013

OTHER PUBLICATIONS

"Digital Image Reconstruction by using Zernike Moments"; Padilla-Vivanco et al.: Aug. 8, 2003 (Year: 2003).*
(Continued)

*Primary Examiner* — John A Pauls
(74) *Attorney, Agent, or Firm* — Young & Thompson (57) ABSTRACT

The subject matter of the present invention is a computer device for tracing (100) surgical instruments ($DM_i$, i being a positive integer) in a hospital environment, said device (100) comprising: —a support platform (10) designed to receive a surgical instrument ($DM_i$, i being a positive integer), a digital camera (20) designed to capture at least one digital image (I) comprising a view from above of at least a portion of the surgical instrument ($DM_i$), an electronic circuit for processing images (30) configured for detecting in said at least one digital image (I) at least one visual characteristic of said surgical instrument ($DM_i$) and for determining at least one piece of visual data (P_PIC) associated with said pictorial element, a digital scale (40) configured to measure the weight of the surgical instrument ($DM_i$) and to determine weight data ($D\_PDS_i$) containing information relating to the measured weight; the present invention also relates to the associated method.

20 Claims, 3 Drawing Sheets

(51) Int. Cl.
  *G06F 16/23*   (2019.01)
  *A61B 90/90*   (2016.01)
  *G16H 40/20*   (2018.01)
  *G06K 9/20*    (2006.01)
  *A61B 90/00*   (2016.01)

(52) U.S. Cl.
  CPC ........ *G16H 40/20* (2018.01); *A61B 2090/061* (2016.02); *A61B 2090/0805* (2016.02); *G06K 9/209* (2013.01)

(56) References Cited

U.S. PATENT DOCUMENTS

| | | | |
|---|---|---|---|
| 6,707,381 B1 | 3/2004 | Maloney | |
| 2004/0186683 A1 | 9/2004 | Farber et al. | |
| 2004/0220692 A1* | 11/2004 | Shenefelt | G05B 19/4207 |
| | | | 700/117 |
| 2006/0184407 A1* | 8/2006 | Ozaki | G06Q 50/22 |
| | | | 705/2 |
| 2008/0185430 A1 | 8/2008 | Goldbach | |
| 2009/0272806 A1 | 11/2009 | Kemp et al. | |
| 2012/0138514 A1* | 6/2012 | Janssens | B07C 5/342 |
| | | | 209/577 |
| 2012/0259582 A1 | 10/2012 | Gloger | |
| 2013/0091679 A1* | 4/2013 | Gloger | G06Q 10/0875 |
| | | | 29/407.04 |

OTHER PUBLICATIONS

International Search Report, dated Sep. 8, 2014, from corresponding PCT Application.

* cited by examiner

TRACEABILITY OF SURGICAL INSTRUMENTS IN A HOSPITAL ENVIRONMENT

TECHNICAL FIELD AND PRIOR ART

The subject matter of the present invention relates to the field of health safety, and relates more specifically to the traceability and tracking of surgical instruments in a medical environment such as a hospital setting.

The objective of the subject matter of the present invention is to respond to different safety and medical standards which have come into effect with regard to the traceability and tracking of (unmarked) surgical instruments in hospital environments, such as hospitals or clinics.

Naturally, the present invention can be used particularly advantageously in hospitals or clinics for tracing and tracking surgical instruments and for reassembling a surgical kit composed of a plurality of surgical instruments.

The present invention can also be applied advantageously in other settings, in veterinary clinics or dental practices for example.

A surgical instrument is defined in the present invention in the following description to mean any type of medical instrument or device designed to be used by a practitioner such as a doctor or surgeon during a medical or surgical intervention. A non-limiting example of such a device could be an ancillary instrument, a scalpel blade, a clamp (haemostatic clamp, cystoscopic clamp, forceps, intestinal clamp etc.), a screw, ligature instrument, spreader or even a probe.

Hospitals and clinics increasingly have to comply with regulations that govern the medical safety of patients.

Said regulations include instruction DGS/R13/2011/449 of 1 Dec. 2011 which recommends the unitary traceability of reusable medical devices to combat Creutzfeldt-Jakob type infections and variations thereof.

Of course, the surgical instruments referred to in the present invention consist of reusable medical devices.

More particularly, this instruction ensures the continuity of Circular "138" from 2001 which requires the traceability of a surgical instrument for the last five patients.

Decree no. 2006-1497 specifies in particular the definition of the traceability of medical devices by defining "the specific rules for materiovigilance applied to certain devices". The text of said decree specifies that materiovigilance comprises rules of traceability from the time a medical device arrives at the hospital setting until the latter is used on the patient.

Today, the traceability of surgical instruments is mainly guaranteed by two approaches.

According to a first approach, the operator responsible for traceability (generally referred to as the pharmacist) has to visually identify each surgical instrument using his own expertise and/or by referring to photographs.

He then manually enters the reference number of the instrument into a computer system which enables the surgical instruments to be tracked in the hospital setting; after entering this reference the positions each instrument in a surgical kit for use in a future operation in the operating theatre.

This approach is time-consuming and tedious.

Furthermore, an approach of this kind does not comply with the new medical requirements mentioned above, as the risk of human error during the visual identification of instruments is not negligible.

A second approach consists of using an optical reader such as a "WhiteReader®" for reading a 2D code (for example a "DataMatrix" type code) which is marked or engraved directly onto each surgical instrument. Alternatively, it is also possible to use RFID labels adhered to the surgical instrument for identification.

Then, after said reading, the computer system automatically identifies the instrument according to information contained in the code or on the label; the reference of the instrument and corresponding information are then integrated automatically into the system.

The Applicant considers that such an approach has limitations, in particular owing to the fact that it applies exclusively to surgical instruments that are "marked", either by engraving or applying a 2D code or by adhering an RFID label.

However, surgical instruments have varying shapes and dimensions which can prevent this type of marking. The Applicant also considers that it is often very difficult to read 2D codes correctly, particularly when the instruments are being used in a surgical intervention (the code may be covered in blood).

Codes also deteriorate over time; for example as a result of wear from sterilisation cycles.

Furthermore, surgical instruments generally have technical surfaces which are impossible to engrave or mark with a code or cover with an adhesive RFID label, without altering their function.

It has also been observed that certain surgical instruments such as ancillary instruments are designed specifically for particular interventions: said instruments are generally loaned by manufacturers to surgeons who insert implants purchased from said manufacturers for example. In cases of this kind, the ancillary instruments often remain the property of the manufacturers and can therefore not be marked in an indelible manner by hospitals or clinics.

Document US 2012/0259582 relates to unmarked surgical instruments and proposes an approach for addressing, at least partly, the various disadvantages mentioned above.

In particular, this document proposes the use of a platform which integrates a plurality of weight sensors which can establish a "geographic" distribution of the weight of a surgical instrument placed on the platform.

Said platform is combined with a computer system comprising a previously created database which stores information relating to the distribution of weight of a plurality of predetermined surgical instruments. It is thus possible, with knowledge of this distribution, to determine the instrument placed on the platform.

However, the Applicant considers that this approach, although interesting, is only adapted to "flat" instruments such as those shown in FIGS. 6 to 12 of said document US 2012/0259582.

In fact, according to this approach, the identification of the surgical instrument depends directly on the manner in which the instrument is placed on the platform.

Thus, the solution proposed in this document is not suitable for surgical instruments with a three-dimensional shape and several bearing faces and which can thus be placed down on several faces.

Document US 2004/0186683 proposes using a combination of a camera and weight sensors. However, the camera is used essentially for identifying in real time an instrument that has just been picked up by a surgeon during an operation.

In fact, according to this approach it is necessary to position each type of instrument in a predefined location. When an instrument is removed from its location the latter is detected by the camera.

With this approach it is necessary to have a large number of locations as an ancillary kit generally contains a large variety of instruments; the technical solution recommended in this document US 2004/0186683 is not adapted to the reality of the field.

Moreover, said solution is of interest for tracking instruments during surgical intervention; however, the latter is not provided for reassembling a surgical kit after an operation.

The prior art does not propose an entirely satisfactory solution which makes it possible to guarantee at any time and in all circumstances the traceability of the surgical instruments in a hospital setting.

SUBJECT MATTER AND SUMMARY OF THE PRESENT INVENTION

The subject matter of the present invention aims to improve the current situation described above.

The subject matter of the present invention aims to overcome the various disadvantages mentioned above by proposing a method for tracing surgical instruments in a hospital setting, such a method being provided for example for reassembling a surgical kit composed of one or more surgical instruments.

According to the present invention, the method is implemented by computer processing and comprises in particular an acquisition phase and a processing phase.

In particular, the acquisition phase according to the present invention comprises the following steps:
positioning a surgical instrument on a support platform;
capturing, by means of a digital camera positioned above the support platform, at least one digital image comprising a view from above of at least one portion of the surgical instrument; and
processing images for detecting in said at least one digital image at least one visual characteristic of the surgical instrument and for determining at least one piece of visual data associated with said visual characteristic.

The acquisition phase also comprises measuring the weight of the surgical instrument using a digital scale such as precision digital scale, in order to obtain data relating to weight which contains information relating to the measured weight.

Following this acquisition phase the method comprises a processing phase comprising the identification of the surgical instrument.

More particularly, said identification consists in particular of comparing the weight data and the visual data with a predetermined data base establishing a link between at least one surgical instrument and information relating to the weight and to one or more visual characteristics of said at least one surgical instrument.

This identification also consists of determining, as a function of this comparison, identification data containing information relating to the identity of the surgical instrument placed on the support platform.

Preferably, this comparison consists of comparing each piece of weight data with all of the weight data contained in the database, and calculating the "distance" between the measured weight data and each of the pieces of weight data in the database; in the same way, each piece of visual data is compared with all of the visual data contained in the database for calculating the "distance" between the measured visual data and each piece of data.

These calculated "distances" can possibly be weighted, for example if it is considered that the measured visual characteristic or characteristics are more discriminating than the measured weight.

All of these calculated (and possibly weighted) distances make it possible to determine a list of candidates classified according to confidence index which is a function of said "distances".

The determination of the identification data then consists of selecting the candidate with the smallest "distance"; that is the candidate which has the best confidence score for the identification of the instrument.

This distance can be calculated for example by calculating the absolute value of a difference, or even by calculating the ratio of the two values. A person skilled in the art would understand here that other formulae can also be selected for calculating this "distance".

Thus, this succession of technical stages which is characteristic of the present invention makes it possible to automatically identify surgical instruments to ensure their tracking and traceability, for example to correctly reassemble a surgical kit.

Said identification does not require any marking or functional alteration of surgical instruments, and makes it possible to cleverly overcome the disadvantages identified in the prior art described above.

The use of image processing techniques makes it possible to determine here in a precise manner the intrinsic characteristics of the surgical instrument, such as for example its form, its dimensions, its contours or even its colour.

The weight measurement then makes it possible to determine another intrinsic characteristic of the surgical instrument.

The association of these intrinsic characteristics, particular to the instrument, makes it possible to identify the instrument with a high level of precision.

This identification implies that the database comprises information relating to visual characteristics and to the weight of each surgical instrument.

The method according to the invention preferably includes a stage of teaching for the formation of said database which is used as a reference for the identification of the instruments.

Over the course of this teaching the operator can then enter the weight of all of the surgical instruments available to him and take the pictures of these instruments which he is registering and check their visual characteristics. Thus the method according to the invention comprises a preliminary teaching stage during which the database is created for each surgical instrument determined, the said intrinsic information relating to the weight and the visual characteristics of said surgical instrument.

During this teaching phase each instrument is referenced by its own particular characteristics: weight, form, colour, contour, impedance, etc.

Advantageously, the database can also be updated when a new instrument becomes available (for example during an update), or following a validation of the identification.

In another variant it is possible to ensure than the database is a centralised database connected to a remote server; in this case, the identification stage comprises the remote querying of said database.

The fact of moving the administration and the management of said database makes it possible to have an up-to-date database. The updating of said database is centralised which limits the responsibility of the user and reduces the health risks associated with an incorrect identification which may be caused by a database which is not up-to-date.

Advantageously, the support platform on which the surgical instrument is placed has a diffusing quality; i.e. it allows light to pass through it or more particularly allows the diffusion of light.

Preferably, the acquisition phase comprises backlighting the surgical instrument by emitting a backlight through the support platform in the direction of the digital camera.

Said backlighting makes it possible advantageously to show the silhouette of the surgical instrument and avoid in particular areas of shade which could alter the detected form of the instrument and introduce an error into the identification.

This kind of backlighting is advantageous for example during the measurement of certain characteristics such as the form or contours. Of course, the measurement of the visual characteristic relating to the colour of the instrument does not require this backlighting.

Said backlighting is preferably emitted vertically; i.e. in a direction substantially perpendicular to the plane formed by the platform. This orientation ensures that the shape of the instrument placed on the platform is not deformed. It should also be noted that said backlight is emitted in the direction of the digital camera which is positioned above the platform.

Advantageously, the backlight has a wavelength between in the order of 400 and 500 nanometres; preferably, said wavelength is 470 nanometres.

Advantageously, the scale is configured to cover a weight range between 0 and 10 kilograms, preferably with precision of between 0 and 1 gram.

Preferably, the acquisition phase also comprises the polarisation of the backlight by a diffusion film covering the support platform for homogenising the diffusion of the backlight passing through said platform.

This polarisation thus makes it possible to homogenise the light in the field of vision of the digital camera.

More particularly, said backlight is diffused in a single direction, which is preferably that of the camera. This is referred to as a unidirectional diffusing film.

This prevents the operator being dazzled.

Preferably, the unidirectional diffusing film is configured to allow the diffusion of the backlighting through the platform in a direction perpendicular to the plane defined by the support platform.

In one variant, the acquisition phase also comprises the measurement of another physical dimension characteristic of the surgical instrument.

In this variant, the identification comprises the verification of the identification data as a function of said measured dimension; here the database comprises for each surgical instrument predetermined information relating to said physical dimension.

Advantageously, said physical dimension corresponds to an electrical characteristic of the instrument such as its impedance.

In this variant, it is clear that the impedance also makes it possible by means of the database to characterise and identify the surgical instrument.

A person skilled in the art would understand here that other dimensions can be measured during said acquisition phase.

The various different embodiments described above make it possible to discriminate between intrinsic characteristics of instruments to identify with precision the surgical instrument placed on the platform. This identification is then subjected to a manual validation by the user.

Said manual validation makes it possible to enhance the precision of the database during its use.

A combination of the different methods of acquisition described above is also possible, as well as verification means which calculate a confidence index of the results of the identification enabling a user to have an idea about the reliability of the result.

These means can also be configured to weight the results of each identification as a function of each variable measured to obtain a final precise identification. For example, if the results of the identification by visual characteristics and weight value are the same, then the identification is validated.

Advantageously, the processing phase can comprise a previous phase of gathering the weight data and the visual data.

One of the other objectives of the present invention is to enable the preparation of surgical instruments intended to be used for surgical intervention.

Before such an intervention, the different surgical instruments required for the intervention are assembled as a unit into a kit after sterilisation.

It is necessary to have a precise knowledge of the different instruments in the kit as well as the history of their preceding use.

It is also essential for each instrument to be correctly positioned in the kit in its designated location to facilitate handling during the intervention.

Thus the database comprises advantageously for each surgical instrument localisation data containing information relating to a predetermined location of the surgical instrument in the surgical kit.

According to the present invention, the method comprises a reassembly phase comprising a localisation stage during which the positioning of the surgical instrument into the surgical kit is determined as a function of said localisation data.

Advantageously, the method according to the invention also comprises a tracking stage which consists of assigning to the identification data information relating to the use of the instrument. This makes it possible for example to report an instrument when the latter has been used during a surgical intervention, or to report an instrument when the latter has been sterilised prior to the surgical intervention.

It is thus possible to establish a history of events related to a surgical instrument for example by reporting the latter as "used" or "unused", and/or by reporting the latter as "sterilised" or "unsterilised".

Preferably, the reassembly phase also comprises a display stage which consists of displaying on a digital screen in the form of a digital tablet a digital inventory of the surgical kit as well as the associated surgical instruments according to their predetermined position.

The display of such an inventory is advantageous in that it makes it possible to easily visualise the kit and the associated instruments. The display of the positioning is also used to indicate the "status" of the reassembly, by listing the instruments which have already been placed in the kit and those which have not, so as to visualise the potentially missing instruments (which could have been left in the washing unit or even thrown in the bin accidentally, etc.).

Preferably, the digital screen is a touch screen and it is possible to select the desired instrument manually on the screen, for example when the practitioner performing the operation is using the instrument.

Correlatively, the subject matter of the present invention relates to a computer program which comprises instructions adapted to the execution of the stages of the method as described above, in particular when said computer program is executed by at least one processor.

A computer program of this kind can use any programming language and be in the form of a source code, an object code, or an intermediary code between a source code and an object code, such as in a partially compiled form or in any other desired form.

Moreover, the subject matter of the present invention relates to a recording medium readable by a computer on which a computer program is recorded comprising instructions for executing the stages of the method as described above.

On the one hand, the recording medium can be any entity or device capable of storing the program. For example, the medium can comprise a storage means, such as a ROM, for example a CD-ROM or microelectronic circuit type ROM, or even a magnetic recording means, for example a floppy disc or hard disc (mass storage: hard disk or USB stick).

On the other hand, said recording medium can also be a transmissible medium such as an electric or optical signal, a signal of this kind able to be sent via an electric or optical cable, by terrestrial radio or by self-directing laser beam or other means. The computer program according to the invention can be downloaded in particular to an internet type network.

Alternatively, the recording medium can be an integrated circuit in which the computer program is incorporated, the integrated circuit being adapted to execute or be used in the execution of the method in question.

The subject matter of the present invention also relates to a computer device for tracing surgical instruments in a hospital setting for the reassembly of a surgical kit composed of least one surgical instrument.

The device according to the present invention comprises computer means which are configured for the implementation of the method as described above.

More precisely, the device comprises advantageously:
an acquisition module comprising:
a support platform designed to receive a single surgical instrument,
a digital camera, positioned above the support platform, configured to capture at least one digital image comprising a view from above of at least a portion of the surgical instrument,
an electronic circuit for processing images configured for detecting in said at least one digital image at least one visual characteristic of said surgical instrument and for determining at least one piece of visual data associated with said characteristic,
a digital scale configured to measure the weight of the surgical instrument and for determining weight data containing information relating to the measured weight;
a processing module comprising:
an electronic identification circuit configured on the one hand for comparing the weight data and the visual data with a predetermined database establishing a link between at least one surgical instrument and information relating to the weight and the visual characteristic of said at least one surgical instrument, and on the other hand for determining as a function of said comparison and the database at least one piece of identification data containing information relating to the identity of said surgical instrument.

Thus, the present invention, by combining its functional and structural characteristics, enables the tracking and tracing of surgical instruments in a hospital setting while guaranteeing in particular the correctness and completeness of the instruments positioned in a kit.

BRIEF DESCRIPTION OF THE ACCOMPANYING FIGURES

Other characteristics and advantages of the present invention are given in the following description, with reference to the accompanying FIGS. 1 to 3 which illustrate an example which should not be considered to be limiting in any way, and in which.

DETAILED DESCRIPTION OF AN EMBODIMENT OF THE INVENTION

A method for tracing surgical instruments in a hospital setting as well as the associated device are described in the following by referring jointly to FIGS. 1 to 3.

One of the objectives of the present invention is to enable the tracing of surgical instruments by overcoming the various disadvantages of the prior art identified above.

The present invention provides the operator in charge of reassembling a surgical kit KT with a simple and easy-to-use tool which consists of a tracking device 100; said device 100 enabling a precise identification of surgical instruments $DM_i$, (i being a positive integer) by using physical information which is characteristic of the instruments.

Here the variable i is 3 to simplify the example described in the figures.

Thus, in this example there are surgical instruments $DM_1$, $DM_2$, and $DM_3$.

Figure 1:
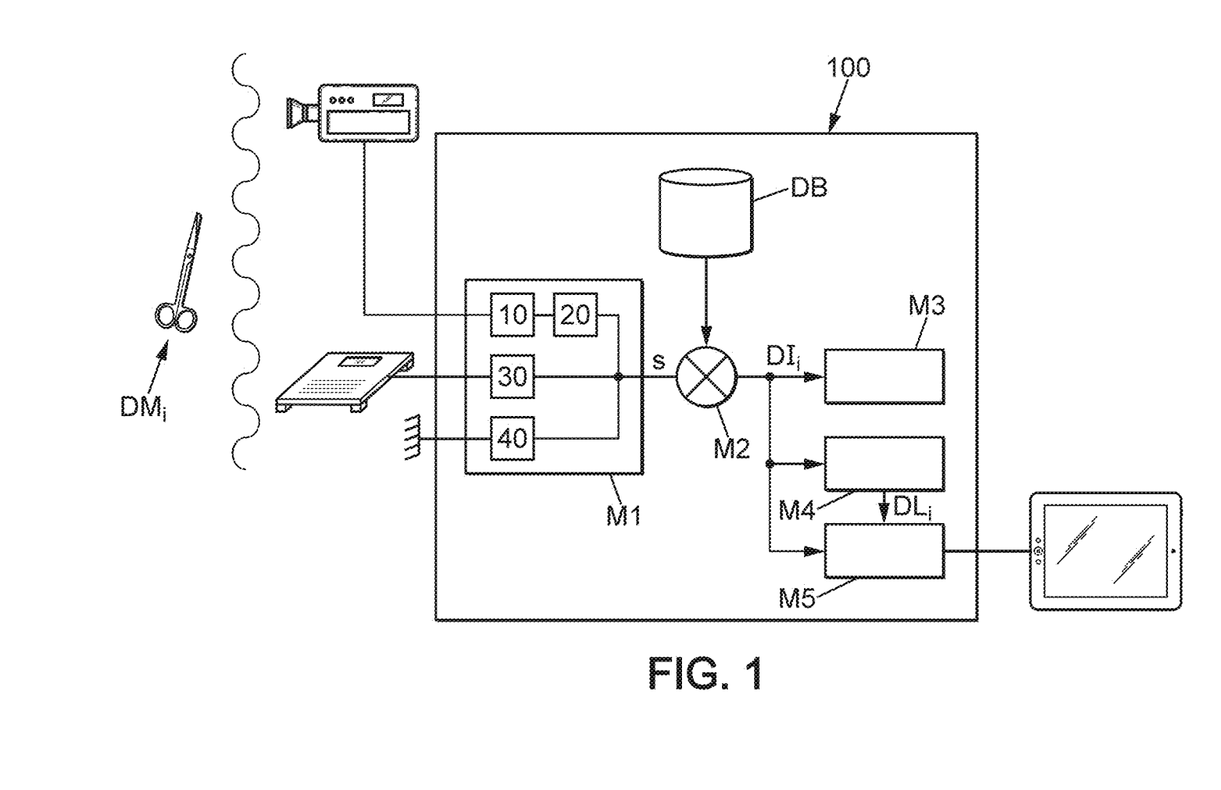
FIG. 1 represents in a schematic manner a device for tracing surgical instruments according to an advantageous embodiment of the present invention.

In this example and as illustrated in FIG. 1, in stage S1 the operator positions the surgical instrument that he has to identify, here $DM_1$, on a support platform 10. Preferably, said platform 10 has a curved shape (not shown here) to prevent the device falling on the ground and getting damaged.

Once positioned on said platform 10 the operator activates the device 100.

More particularly, the device 100 comprises an acquisition module M1 configured during an acquisition phase P1 to acquire a plurality of signals of an electrical nature, each containing information relating to an intrinsic characteristic of the surgical instrument placed on the support platform 10; i.e. a characteristic of the instrument which makes it possible to identify said instrument.

The various information contained in each of the electrical signals is then used during a second phase referred to as process P1.

One of the first aspects of the present invention consists of using the visual characteristics of the instrument $DM_1$ placed on the platform 10; this can be for example the shape of the instrument, its contour, a specific radius of curvature, each of said pictorial elements being able to characterise the instrument $DM_1$.

Thus, in the example described here, the acquisition module M1 comprises a digital camera 20 and an electronic circuit for processing images 30, such as an image processor configured for processing images.

According to the present invention, the latter can be a 2D camera or a 3D camera (for example a time-of-flight camera or a structured light scanner).

In the example described here, the camera 20 makes it possible to acquire an image I of the instrument $DM_1$ during stage S4.

Prior to this acquisition stage S4, the acquisition module M1 includes the emission of a light source LUX, i.e. backlighting, during stage S2 by a plurality of LEDs 50; said LEDs 50 are positioned underneath the platform 10 and emit a backlight LUX through the platform 10.

Of course in this example, the platform 10 is diffusing; it thus allows the diffusion of backlighting.

In the example described here, the emission of said light LUX is perpendicular to the direction of the camera 20.

This backlighting S2 thus makes it possible to avoid shaded areas in the field of vision of the camera 20.

In the example described here, the wavelength of this backlight LUX is substantially 470 nanometres. This wavelength has the advantage of ensuring good stability of the ambient light during the capture of the image S4; it also makes it possible to correctly remove contrasts in the working environment.

In order to homogenise said light LUX in the field of vision of the camera 20 to obtain a clear image, the platform 10 is covered with a diffusing film 11 which enables the polarisation S3 of light LUX in the same direction.

This is referred to as a unidirectional diffusing film.

Preferably, said unidirectional diffusing film 11 is designed to diffuse light substantially in the direction of the camera 20; i.e. here perpendicular to the platform 10.

This polarisation of light prevents in particular the operator being dazzled.

By means of this backlighting S2 and this polarisation S3, the image I captured by the camera 20 is clear and reveals the form of the instrument $DM_1$ avoiding shaded areas.

In order to identify in this digital image I one or more visual characteristics of the surgical instrument $DM_1$, the electronic circuit for processing images 30 is configured to process images S5 making it possible to detect and extract visual characteristics in the image I; the electronic circuit 20 is thus configured to use techniques for processing images such as for example background extraction techniques and/or to determine coefficients of description of forms such as for example Zernike or Hue, or contours.

Alternatively and/or in a complementary manner it can be performed by calculating the dimensions.

This recognition S5 can also be performed by recognising "local" characteristics, for example using FAST or MSER.

In the example described, the processor 30 is also configured to use information relating to the colorimetric elements of the image I acquired: for example by using a histogram of colours or colorimetric representation.

When placing the instrument $DM_1$ on the platform 10, it is thus possible to determine at least one piece of visual data $D\_PIC_1$ characteristic of the instrument $DM_1$.

The acquisition module M1 makes it possible to use other physical characteristics of the instrument, for example its weight or impedance.

In the example described here and as illustrated in FIG. 1, the acquisition module M1 thus comprises a precision scale 40, integrated into the platform.

Thus when the operator positions the surgical instrument $DM_1$ on the platform 10, he obtains during a stage S6 a piece of data $D\_PDS_1$ containing information relating to the weight of this instrument $DM_1$.

In the example described here, the acquisition module M1 can also use another characteristic of the surgical instrument $DM_1$, for example its impedance.

In this mode, the module M1 thus comprises an electrical measurement means 12 configured to perform a measurement during stage S7 of an electrical signal representative of the impedance of the surgical instrument. By means of this third measure impedance data $D\_IMP_1$ relating to the surgical instrument $DM_1$ is made known.

All of this data $D\_PIC_1$, $D\_PDS_1$, and $D\_IMP_1$ from this acquisition phase P1 are characteristic of the instrument $DM_1$.

Said data is then processed and used during phase P2, referred to as the processing phase, to determine precisely the identity of the instrument placed on the platform 10.

First of all, said data $D\_PIC_1$, $D\_PDS_1$, and $D\_IMP_1$ are gathered during stage S8 by an electronic identification circuit 60.

Once gathered, the instrument $DM_1$ placed on the platform 10 is identified S9.

Said identification S9 comprises a comparison S9_1 by the electronic circuit 60 of the weight data $D\_PDS_1$, the visual data $D\_PIC_1$ and the impedance data $D\_IMP_1$ with a database DB.

Said database DB comprises data about a plurality of instruments $DM_1$, $DM_2$ and $DM_3$ and predetermined information relating to the weight and visual characteristics of each of the surgical instruments.

Said database DB also contains information relating to the impedance of each of these surgical instruments.

In the example described here and as illustrated in FIG. 1, said database DB is removed; it is accessible via a remote server S.

In the example described here and illustrated in FIG. 1, the comparison S9_1 requires previously a query S9_0 via communication means 70 of the server S which is connected to the database DB.

As mentioned above, the fact of removing the administration and management of said database DB to a remote server S makes it possible to have an up-to-date database.

The updating of this database DB is thus centralised, which limits the responsibility of the user and reduces the health risks associated with an incorrect identification caused by a database which is not up-to-date.

Obviously, a person skilled in the art would understand here that the database DB can also be administered locally for each device 100.

This comparison makes it possible to perform "matching", making is possible for the electronic identification circuit 60 to determine during stage S9_2 the identification data containing information relating to the identity of the surgical instrument placed on the platform.

In the example described here, the electronic identification circuit 60 therefore compares the data $D\_PIC_1$, $D\_PDS_1$, and $D\_IMP_1$ from phase P1 with different visual, weight and impedance data of each of the instruments from the database DB.

As mentioned above, during this comparison for each piece of data $D\_PIC_1$, $D\_PDS_1$, and $D\_IMP_1$ from phase P1 the distance is calculated from different visual data, weight and impedance data contained in the database DB.

This comparison makes it possible to establish for each piece of data $D\_PIC_1$, $D\_PDS_1$, and $D\_IMP_1$ a list of possible candidates as a function of the distances calculated (the smallest distance); said calculation of distance providing a confidence index for the identification.

Then a global distance is calculated, as a function of predetermined weighting coefficients.

Ideally, said weighting is 1/n, n being here the amount of data taken into consideration (here 3 items).

By selecting the smallest global distance it is possible to determine the data $DI_1$ which corresponds in the database DB to the instrument $DM_1$; clearly this is a specific example which is given purely by way of illustration and should not to be considered to be limiting in any way.

The electronic identification circuit 60 is capable of automatically determining the identification data $DI_1$, (either $DI_1$, $DI_2$, or $DI_3$) containing information relating to the designation of the instrument $DM_i$ ($DM_1$, $DM_2$, or $DM_3$) placed on the platform 10, as a function of data received the acquisition phase P1.

It is also possible to ensure that the circuit 60 determines a list of candidates proposing the designation of a plurality of instruments $DM_i$, arranged by order of relevance as a function of the calculation of distances and their calculated confidence indexes.

In this case, it is the operator who selects the instrument from this list, according to his particular experience.

This enables continuous teaching; that is the operator can also continue to update the database by validating the identification or completing the information that it contains, for example for adding a new surgical instrument or recording a characteristic that was previously unknown.

In the example described here the electronic identification circuit 60 is also configured to correlate the different identification results for each measured signal, and thus avoid errors of identification; a weighting of these results is considered.

Thus, if the result of the identification is not certain (confidence index lower than a predetermined threshold), for example if the comparison of data relating to visual characteristics and weight with the database ends in an uncertain identification, with a non-negligible degree of error, the system is designed to declare the instrument as unknown, leaving the validation to the operator.

According to the identification the operator will perform the system can update the database and the weighting of the distances of intrinsic characteristics in order to identify with precision the next time the object is the platform.

The electronic identification circuit 60 is thus configured to ensure the effective identification of the surgical instrument placed on the platform, in particular by using data from the acquisition phase, by querying an up-to-date database, and by proceeding to a verification.

One of the other objectives of the present invention is to ensure the tracking and traceability of surgical instruments for their use in an operating set. Said operations form part of a reassembly phase P3 enabling in particular the reassembly of a surgical kit KT.

Figure 2:
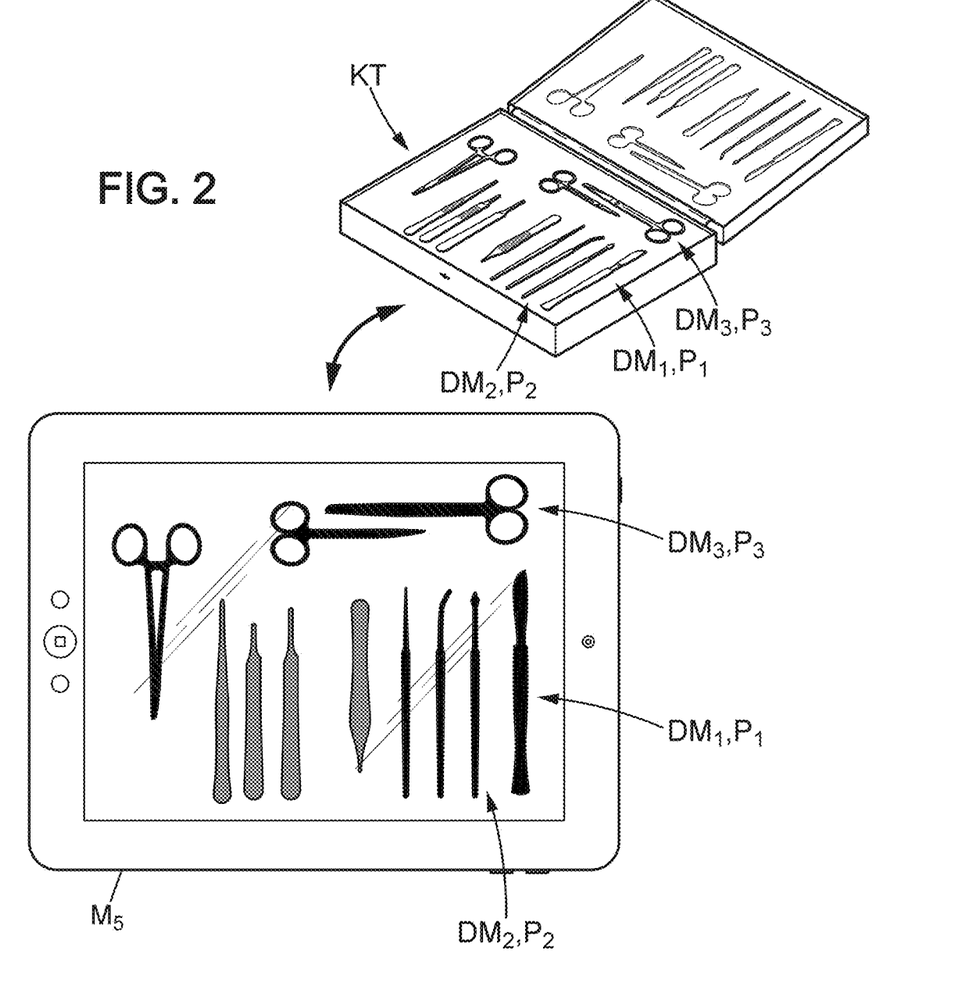
FIG. 2 represents in a schematic manner a non-restrictive example of a digital screen displaying the virtual inventory of a surgical kit and associated medical instruments.
Figure 3:
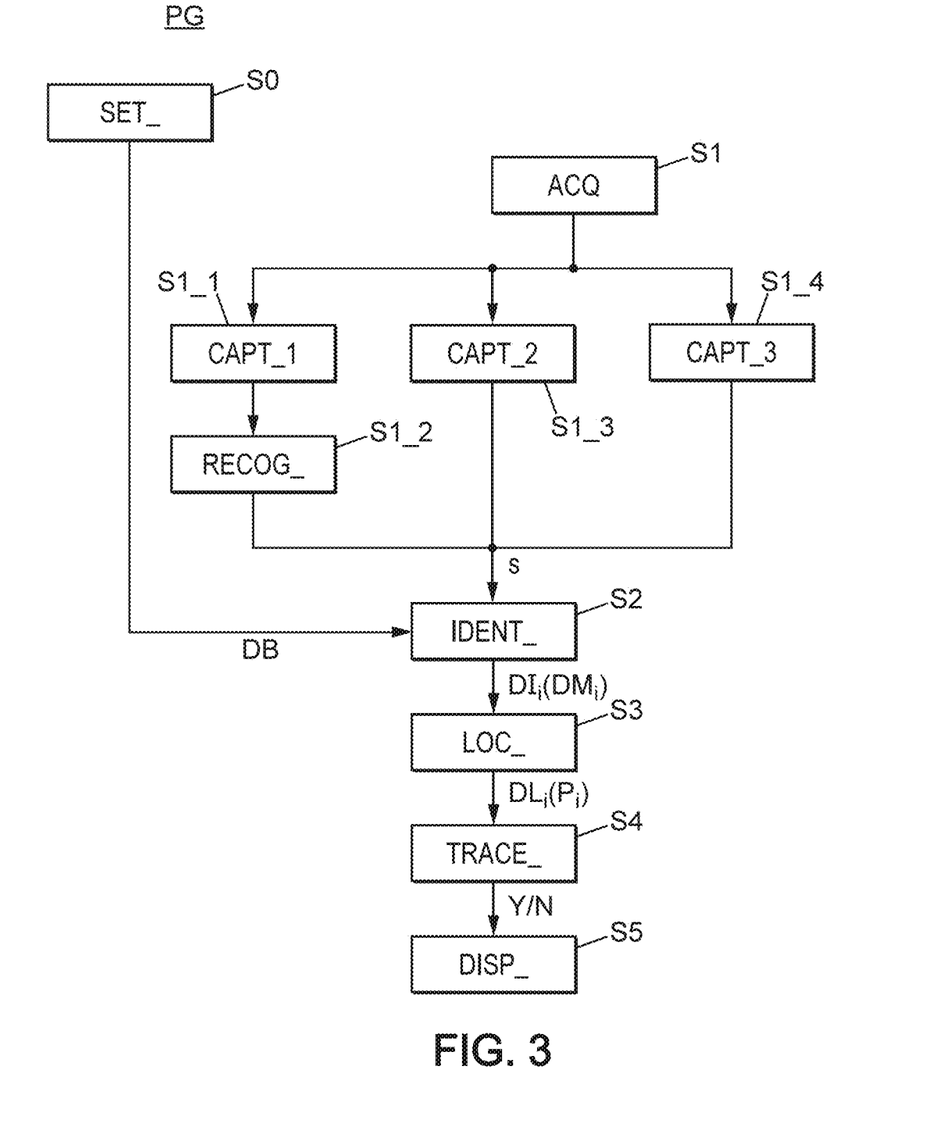
FIG. 3 consists of a flow chart representing the different stages implemented according to an embodiment of the invention.

For this purpose surgical instruments are generally packaged in a kit KT (represented in FIG. 2).

It is therefore necessary to have a correctly assembled kit KT, i.e. a kit KT in which each instrument is positioned in its intended place.

In the example described here and as illustrated here in FIGS. 1 and 2, the database DB comprises localisation data $DL_1$, $DL_2$, $DL_3$ providing a predetermined position $P_1$, $P_2$, $P_3$ in the kit KT for each surgical instrument $DM_1$, $DM_2$, $DM_3$.

In this example and as illustrated in FIGS. 1 and 2, the device 100 comprises a tracing electronic circuit 90 which is configured during a localisation stage S10 for determining the respective position $P_1$, $P_2$, $P_3$ of each surgical instrument $DM_1$, $DM_2$, $DM_3$ in the kit KT as a function of the localisation data $DL_1$, $DL_2$, $DL_3$.

In the example described here and as illustrated here in FIG. 1, said localisation stage S10 comprises tracking during which to each piece of identification data $DI_1$, $DI_2$, $DI_3$ information relating to the respective use of each instrument $DM_1$, $DM_2$, $DM_3$ is assigned for reporting instruments $DM_1$, $DM_2$, $DM_3$ as "used" during surgical intervention or "sterilised".

Thus, each piece of identification data $DI_1$, $DI_2$, $DI_3$ comprises information according to which the instrument $DM_1$, $DM_2$, $DM_3$ has been used or not used (and/or sterilised or not sterilised).

In the example described here, and as illustrated here in FIG. 1, the tracing device 100 comprises display means 80 such as a digital touch screen tablet configured to display, during a display stage S11, a digital inventory of the surgical kit KT as well as the associated surgical devices $DM_1$, $DM_2$, $DM_3$.

As illustrated in FIG. 2, this display makes it possible to visualise during surgical intervention each instrument $DM_1$, $DM_2$, $DM_3$ in the surgical kit KT, with its precise positioning and it history (used and/or sterilised).

By way of example, the shaded instruments in FIG. 2 represent used instruments and the hatched instruments in FIG. 2 represent sterilised and not used instruments.

The different means described above are controlled by a specific computer program PG which comprises instructions adapted for the execution of the stages of the method described above, this program PG is recorded on a recording support C1.

Thus, the present invention as described above provides hospital staff with an innovative solution which complies with new health standards.

The present invention thus proposes a system for recognising a surgical instrument (medical device) without marking from the physical characteristics of the latter. This system aims essentially to overcome the lack of automatic device traceability of ancillary kits, in particular during their reassembly on sterilisation, other medical devices already having mature technology for this.

The present invention is thus particularly suitable for placing in two strategic places: the operating theatre and sterilisation room. In each of these places it has a specific use: in the operating theatre the present invention enables the advance reassembly of the kits KT. More precisely, at the end of an intervention, an operator reassembles the used kit KT prior to sending it for sterilisation. He identifies each of the instruments $DM_i$, before placing them in the kit KT. This makes it possible to anticipate and prepare the reassembly stage during the sterilisation (in this way the reassembly during sterilisation is made easier) as well as tracing the kit when leaving the room. During sterilisation the present invention is used for the reassembly of the kits KT. In similar manner to the use in a theatre, when leaving the sterilisation room an operator has to reassemble the sterilised kit prior to sending it to the operating theatre. Each instrument $DM_i$, is identified one by one by means of the present invention. It is ensured that the kit KT is reassembled prior to sending to the operating theatre which limits unnecessary resterilisation. The traceability when leaving the sterilisation room is also ensured.

The advantage of the present invention is in providing full traceability, without the risk of unnecessary sterilisation and it enables the hospital to evaluate the instruments $DM_i$, in volume and in value.

The present invention can be used for any medical device which needs to be identified and cannot be marked by a code or by a label.

It should be observed that this detailed description relates to a particular embodiment of the present invention, but this description is not limited in any way to the subject matter of the invention; on the contrary it aims to remove any possible imprecision or any incorrect interpretation of the following claims.

The invention claimed is:

1. A method for reassembling a surgical kit, implemented and carried out by a computer in communication with a digital camera and a digital scale provided with a support platform, said surgical kit comprising a plurality of unique surgical instruments, each of said unique surgical instruments being unmarked and unique as to a combination of at least one visual characteristic and weight, said method comprising:
an acquisition phase;
an identification phase; and
a reassembly phase; wherein,
i) the acquisition phase includes, for each surgical instrument of the unique surgical instruments of said surgical kit:
positioning said surgical instrument on the support platform;
capturing, using the digital camera positioned above the support platform, at least one digital image of said surgical instrument, comprising image data of at least one portion of said surgical instrument;
at the computer, detecting in said at least one digital image the at least one visual characteristic of said surgical instrument and determining visual data associated with said visual characteristic; and
using the digital scale to measure the weight of said surgical instrument and obtaining weight data generated by said measuring, the weight data containing information relating to the measured weight of said surgical instrument,
ii) the identification phase includes, for each of the unique surgical instruments of said surgical kit:
at the computer, comparing both the obtained weight data and the captured visual data respectively with weight data and visual data associated with each one of the unique surgical instruments of said surgical kit stored in a database, and
at the computer, determining, as a result of said comparison, at least one piece of identification data identifying said each unique surgical instrument,
iii) the reassembly phase comprises reassembling said surgical kit by placing said each identified individual surgical instrument at a determined position in said surgical kit,
wherein, in the comparing, the computer calculates a first distance between the measured weight data and the weight data of each one of the unique surgical instruments stored in the database, and a second distance is calculated between the measured visual data and the visual data of each one of the unique surgical instruments stored in the database, the computer then using the first and second distances to generate a list of candidates for matching said surgical instrument, said candidates classified according to a confidence index as a function of said first and second distances, and
wherein, in the determining, the at least one piece of identification data identifying said each unique surgical instrument is selected as one among the generated candidates having the smallest of said first and second distances.

2. The method according to claim 1, wherein,
the support platform is configured and operated to allow light to pass through the support platform with the light being diffused,
the acquisition phase comprises backlighting said each unique surgical instrument by emitting a backlight through said support platform and in the direction of said digital camera.

3. The method according to claim 2, wherein the backlight has a wavelength between 400 and 500 nanometres.

4. The method according to claim 3, wherein the acquisition phase comprises a polarisation of the backlight by a unidirectional diffusing film covering support platform for homogenising the diffusion of the backlighting passing through support platform.

5. The method according to claim 2, wherein the acquisition phase comprises a polarisation of the backlight by a unidirectional diffusing film covering support platform for homogenising the diffusion of the backlighting passing through said support platform.

6. The method according to claim 1, wherein the acquisition phase further comprises measuring the impedance of said each unique surgical instrument, and in which the identification takes into account said impedance for determining the identification, said database comprising, for said each unique surgical instrument of the surgical kit, information relating to a predetermined impedance value.

7. The method according to claim 1, wherein the identification phase further comprises a previous gathering of the weight data and the visual data.

8. The method according to claim 1, wherein the database is a centralised database connected to a remote server, and wherein the identification phase comprises querying remotely said database.

9. The method according to claim 1, wherein the database further comprises for said each unique surgical instrument of said surgical kit, a localization data containing information relating to said determined position of said each unique surgical instrument in the surgical kit, the reassembly phase further comprising:
determining from said database, for said each unique surgical instrument, the determined position of said each unique surgical instrument in said surgical kit according to said localization data and said at least one piece of identification data,
displaying, on a digital display, a digital inventory of the surgical kit and an illustration of a positioning of said each unique surgical instrument in said surgical kit according to the determined position, and
said each unique surgical instrument being placed in said surgical kit at said determined position responsive to said illustration.

10. The method according to claim 1, wherein each unique surgical instrument of the surgical kit corresponds to an ancillary instrument.

11. The method according to claim 1, wherein said database further comprises, for said each unique surgical instrument, information representative of at least a use event of said each unique surgical instrument, the reassembly phase further comprising establishing, from the database and said at least one piece of identification data, a history of use events of said each unique surgical instrument of the surgical kit.

12. The method according to claim 1, wherein for each candidate, a global distance is calculated from first and second distances associated with the candidate as a function of predetermined weighting coefficients.

13. The method according to claim 12, wherein said predetermined weighting is 1:2.

14. The method according to claim 1, wherein in the determining, each candidate is displayed to a user arranged in order as a function of respective distances, and said each unique surgical instrument is selected by the user from the displayed list of candidates.

15. The method according to claim 14, wherein information of the selection by the user is stored in the database.

16. A system for reassembling a surgical kit, said surgical kit comprising a plurality of unique surgical instruments, each of said unique surgical instruments being unmarked and unique as to a combination of at least one visual characteristic and weight, said system comprising:
  a computer, in communication with a memory and a database;
  a support platform configured to receive each of the unique surgical instruments of said surgical kit;
  a digital camera positioned above the support platform, configured to capture at least one digital image comprising at least one portion of said each unique surgical instrument; and
  a digital scale configured to measure the weight of said each unique surgical instrument and determine weight data containing information relating to the measured weight,
  the memory having computing code stored thereon that, upon execution by the computer, causes the computer to operate as:
    an image processor that detects in said at least one digital image the at least one visual characteristic of said each unique surgical instrument and determines visual data associated with said visual characteristic,
    an identification module that i) compares the weight data and the visual data stored in the database, said database further comprising information of a mapping between each of the unique surgical instruments and information relating to weight data and visual data specific to each of the unique surgical instruments, and ii) determines according to said comparison at least one piece of identification data identifying said each unique surgical instrument, and
    a tracer that determines a position of said each unique surgical instrument in said surgical kit according to said at least one piece of identification data in a manner so as to guide a user to place each of said surgical instruments at positions corresponding thereto in said surgical kit,
  wherein the computer, in operating to compare the weight data and the visual data as the identification module, calculates a first distance between the measured weight data and the weight data of each one of the unique surgical instruments stored in the database, and calculates a second distance between the measured visual data and the visual data of each one of the unique surgical instruments stored in the database, the computer then using the first and second distances to generate a list of candidates for matching said surgical instrument, said candidates classified according to a confidence index as a function of said first and second distances, and
  wherein the computer, in operating to determine the position of said each unique surgical instrument as the identification module, selects the at least one piece of identification data identifying said each unique surgical instrument as one among the generated candidates having the smallest of said first and second distances.

17. The system according to claim 16,
  wherein the database further comprises, for said each unique surgical instrument of said surgical kit, localization data containing information relating to said determined position of said each unique surgical instrument in the surgical kit,
  wherein the computer, operating as said tracer, is further configured to determine the determined respective position of said each unique surgical instrument in said surgical kit according to said localization data and said at least one piece of identification data, and
  wherein the system further comprises a digital screen configured to display a digital inventory of the surgical kit and an illustration of a positioning of said each unique surgical instrument in said surgical kit according to the determined position.

18. The system according to claim 16, wherein each unique surgical instrument of the surgical kit corresponds to an ancillary instrument.

19. The system according to claim 16, wherein said database further comprises, for said each unique surgical instrument, information representative of at least a use event of said each unique surgical instrument, and the computer, operating as said tracer, is further configured to establish, from the database and said at least one piece of identification data, a history of use events of said each unique surgical instrument of the surgical kit.

20. The system according to claim 16, wherein the system further comprises a display, and said computer is configured to display the determined position of said each unique surgical instrument in said surgical kit.

* * * * *